United States Patent
Yang et al.

(10) Patent No.: US 7,508,223 B1
(45) Date of Patent: Mar. 24, 2009

(54) MULTIHOLE AND MULTIWIRE SENSORS FOR LOCALIZED AND GENERAL CORROSION MONITORING

(75) Inventors: Xiaodong Sun Yang, San Antonio, TX (US); Lietai Yang, San Antonio, TX (US)

(73) Assignee: Corr Instruments, LLC., San Antonio, TX (US)

( * ) Notice: Subject to any disclaimer, the term of this patent is extended or adjusted under 35 U.S.C. 154(b) by 252 days.

(21) Appl. No.: 11/655,535

(22) Filed: Jan. 19, 2007

Related U.S. Application Data (60) Provisional application No. 60/760,702, filed on Jan. 20, 2006.

(51) Int. Cl.
*G01R 27/08* (2006.01)
(52) U.S. Cl. .................................................. 324/700
(58) Field of Classification Search ................. 324/700; 204/404, 412; 205/775.5
See application file for complete search history.

(56) References Cited

U.S. PATENT DOCUMENTS

| | | | |
|---|---|---|---|
| 3,259,461 A | 7/1966 | Griffin, Jr. et al. | |
| 6,132,593 A | 10/2000 | Tan | |
| 6,683,463 B2 | 1/2004 | Yang et al. | |
| 2002/0153907 A1* | 10/2002 | Yang et al. | 324/700 |
| 2003/0189058 A1* | 10/2003 | Liff et al. | 221/13 |
| 2004/0155670 A1* | 8/2004 | Yang et al. | 324/700 |

OTHER PUBLICATIONS

L. Yang and N.i Sridhar, "Monitoring of Localized Corrosion," in ASM Handbook, vol. 13A-Corrosion: Fundamentals, Testing, and Protection, Stephen D. Crammer and Bernard S. Covino, Jr., Eds., ASM International, Materials Park, Ohio, 2003, pp. 519-524, Oct. 2003.
F. Hunkeler and H. Bohni, "Determination of Pit Growth Rates on Aluminium Using A Metal Foil Technique," Corrosion, vol. 37, pp. 645-650 (1981).
A. Sehgal, G. S. Frankel, B. Zoofan, and S. Rokhlin, "Pit Growth Study in Al Alloys by the Foil Penetration Technique," J. Electrochem. Soc., vol. 147, pp. 140-148 (2000).
L. Yang, D. Dunn and G. Cragnolino, "An Improved Method for Real-time and Onlin Corrosion Monitoring Using Coupled Multielectrode Array Sensors," Corrosion/2005, paper No. 05379, (Houston, TX: NACE International, 2005).

* cited by examiner

*Primary Examiner*—Vincent Q Nguyen

(57) ABSTRACT

Methods of using multihole and multiwire sensors to measure general and localized corrosion penetration rates near real time are disclosed. The multihole penetration sensor is included of multiple electrodes embedded in individual cavities that are formed by a metal whose external surface is exposed to a corrosion environment. The distance between the inner surface and the external surface of the cavities (wall thickness) varies from one cavity to the other. The electrical resistance or current between each of the electrodes and a common electrode exposed to the same corrosion environment changes significantly when the wall of the cavity in which the electrode resides is perforated by corrosion and the corrosion medium is in contact with the electrode. The corrosion penetration rate is calculated by dividing the wall thickness of the different cavities by the time it takes to penetrate these cavities.

19 Claims, 15 Drawing Sheets

MULTIHOLE AND MULTIWIRE SENSORS FOR LOCALIZED AND GENERAL CORROSION MONITORING

RELATED PATENT APPLICATION

This application claims the benefit of U.S. Provisional Application No. 60/760,702, filed Jan. 20, 2006, by Xiaodong Sun Yang and Lietai Yang and entitled "Multihole and Multiwire Sensors for Localized and General Corrosion Monitoring."

TECHNICAL FIELD OF THE INVENTION

This invention relates to a method for measuring localized and general corrosion penetration rates using sensors consisting of multiple holes or multiple wires.

BACKGROUND OF THE INVENTION

Localized corrosion monitoring has been a challenge to corrosion engineers and plant operators, because most of the presently available corrosion monitoring techniques are for general corrosion, but not sensitive enough for localized corrosion (see L. Yang and N. Sridhar, "Monitoring of Localized Corrosion," in ASM Handbook, Volume 13A-Corrosion: Fundamentals, Testing, and Protection, Stephen D. Crammer and Bernard S. Covino, Jr., Eds., ASM International, Materials Park, Ohio, 2003, pp 519-524). Electrochemical coupled multielectrode array sensors (see U.S. Pat. No. 6,683,463 and No. 6,132,593) have been used for monitoring localized corrosion rates. With the coupled multielectrode array sensors, the localized corrosion rate was derived from the external anodic currents flowing into the anodic electrodes. In less-corrosive environments, the corrosion current may not always be equal to the external anodic current flowing into the anodic electrode in a multielectrode array sensor [see L. Yang, D. Dunn and G. Cragnolino, "An Improved Method for Real-time and Online Corrosion Monitoring Using Coupled Multielectrode Array Sensors," CORROSION/2005, paper no. 05379, (Houston, Tex.: NACE International, 2005)]. It is highly desirable to have an independent method to verify the localized corrosion rates obtained from the coupled multielectrode array sensor or to independently measure the localized corrosion rate in these environments.

Two-electrode penetration devices were reported for corrosion monitoring 40 years ago (see U.S. Pat. No. 3,259,461). In the two-electrode penetration device, a metal specimen was machined into the shape of a liquid container with a known wall thickness. The container was filled with a non-corrosive or less-corrosive liquid (distilled water, for example). The conductivity of the liquid inside the container was measured. During the test, the container was immersed in a corrosive medium to measure the corrosion of the specimen in the medium. When the specimen was perforated by the corrosive medium, the conductivity of the liquid inside the specimen would increase, because the conductivity of the corrosive medium is usually much higher than that of the less-corrosive liquid. The corrosion rate was calculated by dividing the wall thickness of the specimen container by the time needed for the corrosive medium to perforate the specimen wall. Similar penetration concepts using single-layer and single-thickness of specimens were also used to study the pitting corrosion of aluminium foil [see F. Hunkeler and H. Bohni, "Determination of Pit Growth Rates on Aluminium Using A Metal Foil Technique," Corrosion, Vol 37, pp. 645-650 (1981) and A. Sehgal, et al., "Pit Growth Study in Al Alloys by the Foil Penetration Technique," J. Electrochem. Soc., Vol 147, pp. 140-148 (2000)].

These single-layer and single thickness penetration detection devices are excellent for studying corrosion in laboratories, because they not only measure general corrosion, but also measure localized corrosion, such as pitting corrosion. However, they cannot be used as real time sensors to track the changes of corrosivity or the progress of corrosion damages to a system component in the field, because they can only provide a single measurement of a corrosion rate. The present invention describes a method that incorporates a large number of similar specimens that have different wall thickness into an integrated unit that provide a large number of measurements at different times. Therefore, this type of integrated unit is suitable for corrosion monitoring, especially for localized corrosion penetration rate measurements near real-time.

| REFERENCE NUMBERS OF DRAWINGS | |
|---|---|
| 10 | Common electrode |
| 20 | Multichannel impedance meter |
| 25 | Multichannel ammeter, zero-resistance ammeter or other current-measuring unit |
| 26 | Multichannel voltmeter, or other voltage-measuring device |
| 30 | Multiple electrodes |
| 31 | First of multiple electrodes |
| 32 | Last of multiple electrodes |
| 40 | Multiple holes, each accommodating one of the multiple electrodes |
| 41 | First of multiple holes |
| 42 | Last of multiple holes |
| 50 | Metal of interest whose corrosion rate is to be measured |

-continued

REFERENCE NUMBERS OF DRAWINGS

- 60  Corrosive medium (electrolyte)
- 70  Flat surface in parallel with multiple holes
- 71  Surface in parallel with multiple holes
- 80  Insulating spacer for electrically isolating electrodes 30 from the wall of the holes, but allowing the corrosive medium to contact the electrodes so that the impedance measured by 20 is low or current measured by 25 is high if the hole is filled by the corrosive medium
- 90  Thickness of wall (d) between multiple holes 40 and flat surface 70 (or 71). The d value for the first hole is smallest and the d value for the last hole is largest. When corrosion penetrates the wall, the corrosive medium would fill the hole.
- 95  Epoxy or other sealant
- 96  Protection tube or epoxy for inserting the probe into a process stream
- 100 Multiple metal tubes whose corrosion rate is to be measured; each accommodates one of the multiple electrodes 30
- 101 First of multiple tubes
- 102 Last of multiple tubes
- 105 Epoxy or other sealants or weldments
- 106 Epoxy or other sealants to seal the cavities formed by each layer of the spiral-wound foil or sheet.
- 109 Multiple metal tubes whose corrosion rate is to be measured. The tubes are stacked together and the bottom end of each tube is closed or sealed with epoxy or other sealants. Each tube accommodates one of the multiple electrodes 30.
- 110 Multiple metal tubes whose corrosion rate is to be measured. The tubes are formed by spirally winding a piece of large foil into a cylindrical form and sealed at one side and at the end with epoxy or other sealants 105 and 106.
- 111 The smallest of multiple tubes
- 112 The largest of multiple tubes
- 115 Multiple metal foil disks or sheets whose corrosion rate is to be measured.
- 116 The first layer of multiple sheets
- 117 The last of multiple sheets
- 120 Multiple wires whose corrosion rate is to be measured
- 121 First of multiple wires (thinnest)
- 122 Last of multiple wires (thickest)
- 130 Joints of multiple wires to the common electrode
- 150 Single impedance meter
- 160 Multiple impedance boxes, each having a unique value or characteristics
- 161 First of multiple impedance boxes with a unique value
- 162 Last of multiple impedance boxes with a unique value

DETAILED DESCRIPTIONS OF THE INVENTION

Figure 1:
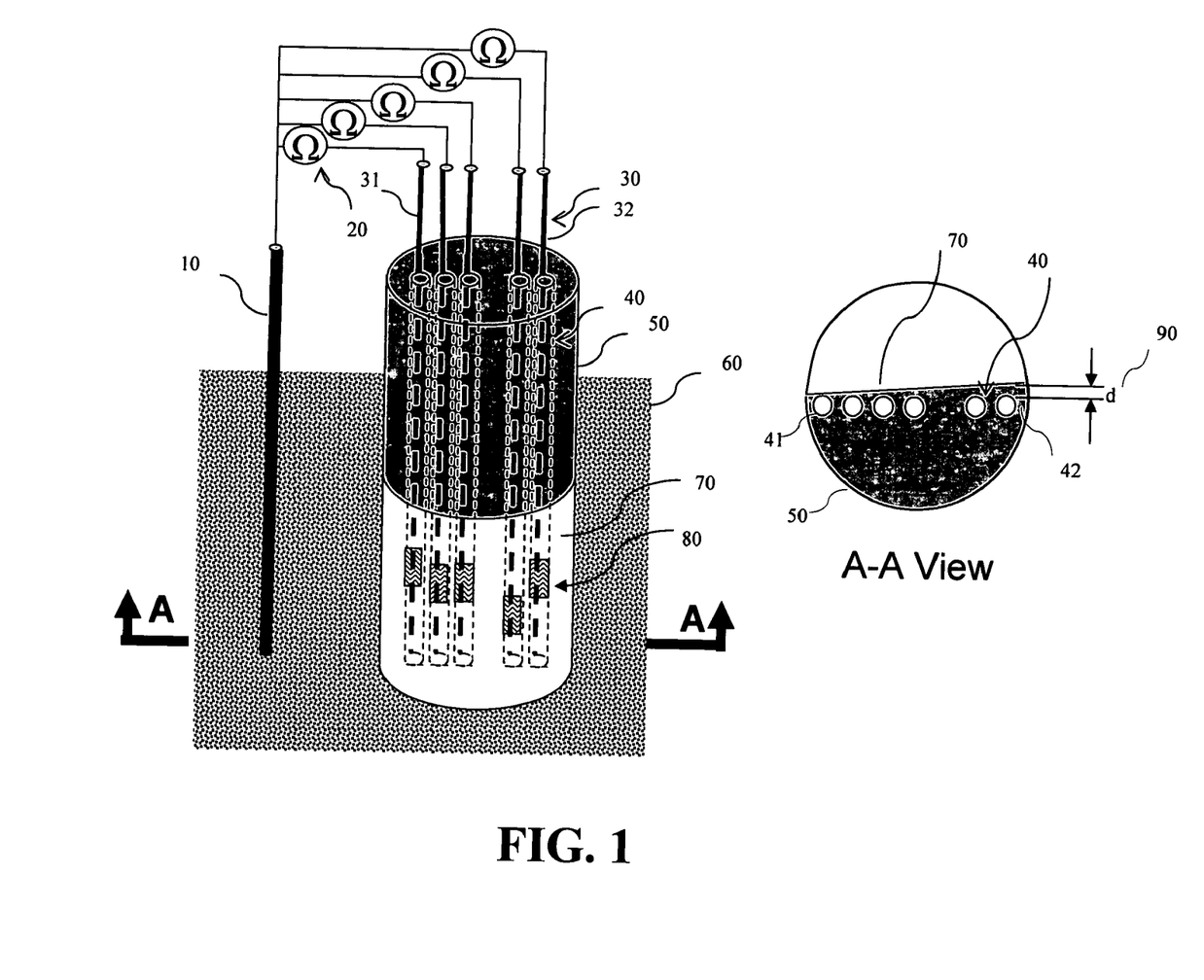
FIG. 1 illustrates the principle of a multihole corrosion sensor.
Figure 2:
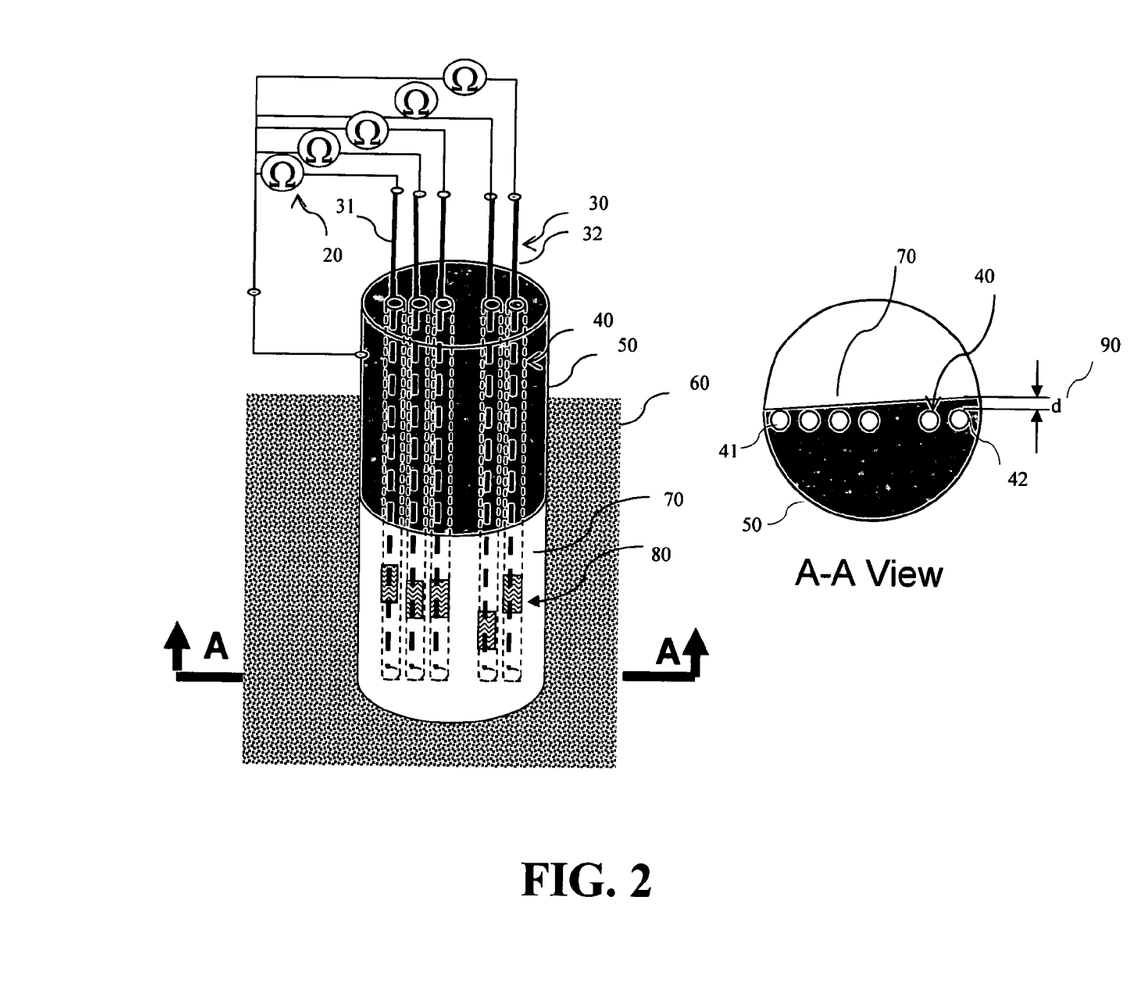
FIG. 2 illustrates the principle of a multihole corrosion sensor without additional common electrode.

FIGS. 1 and 2

FIG. 1 shows a schematic diagram of a device for measuring corrosion penetrations of a metal of interest 50 in an electrolyte (corrosive medium) 60. The metal of interest 50 has a cylindrical form and multiple holes 40 drilled from the top of the metal in parallel to the axial direction of the cylindrical metal (not drilled through). A surface 70 is machined, with a precision machining means, in parallel to multiple holes 40 such that the distance (d) from the first hole 41 is close (e.g., several micrometers) to the surface and the distance from the last hole 42 is far (e.g., up to several millimeters) from the surface 70. One of the multiple electrodes 30 is placed inside each of the holes. The electrodes may be sealed to the holes at the top of the metal of interest 50. Each electrode is connected, through an individual ohmmeter or one channel of a multichannel ohmmeter 20, to a common electrode 10 placed in the same corrosive medium 60. Insulating spacers 80 are used to electrically isolate electrodes 30 from the walls of the holes, but to allow the corrosive medium to contact the electrodes if the hole is filled with the corrosive medium. The holes are initially dry, and the impedance measured by the ohmmeter 20 should be high. If the metal thickness between holes 40 and metal surface 70 is perforated by corrosion (localized corrosion such as pitting, or uniform corrosion), the corrosive medium will leak into the holes and cause the impedance measured by ohmmeter 20 to be low. The corrosion penetration rate can be calculated by measuring the time it takes for each electrode to respond (decreasing) and knowing the d values between the corresponding holes and the surface 70.

This type of corrosion penetration device is responsive to both localized and general corrosion. In the case with localized corrosion, a single pit through the thickness of the wall (d), between one of the holes 40 and the surface 70, would cause the filling of the corresponding hole by the corrosive medium and the response of the impedance signal from the corresponding electrode.

FIG. 2 shows a variation of FIG. 1 where the common electrode is replaced by the main body of the metal of interest 50.

Figure 3:
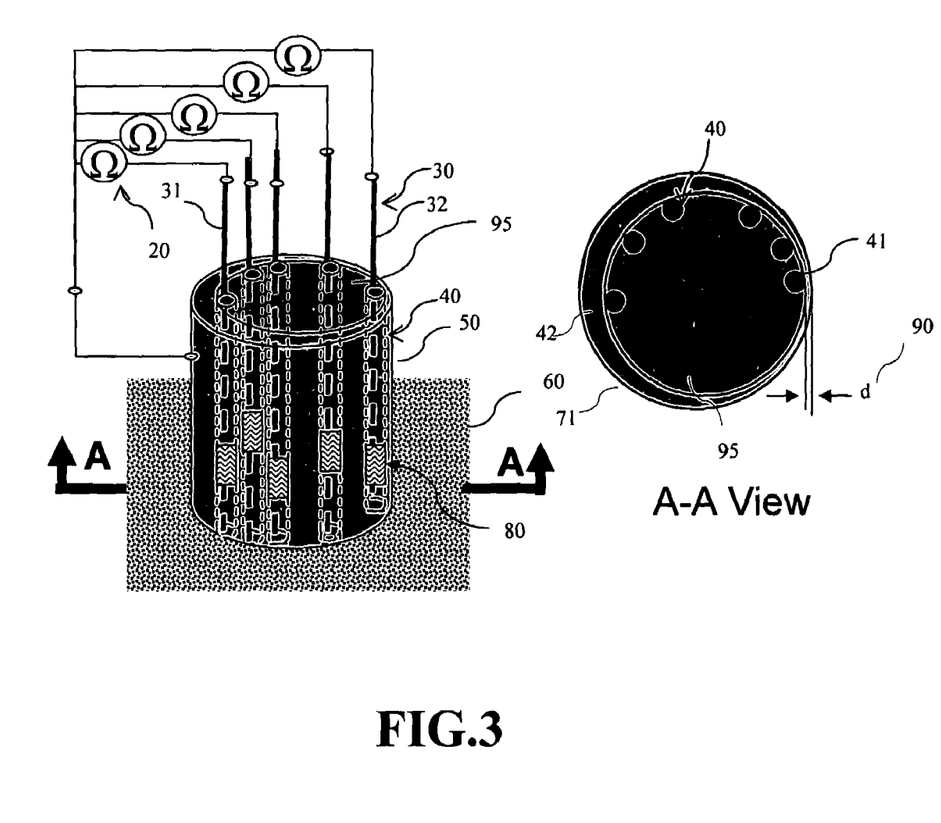
FIG. 3 illustrates the principle of a multihole corrosion sensor with a circular surface.
Figure 4:
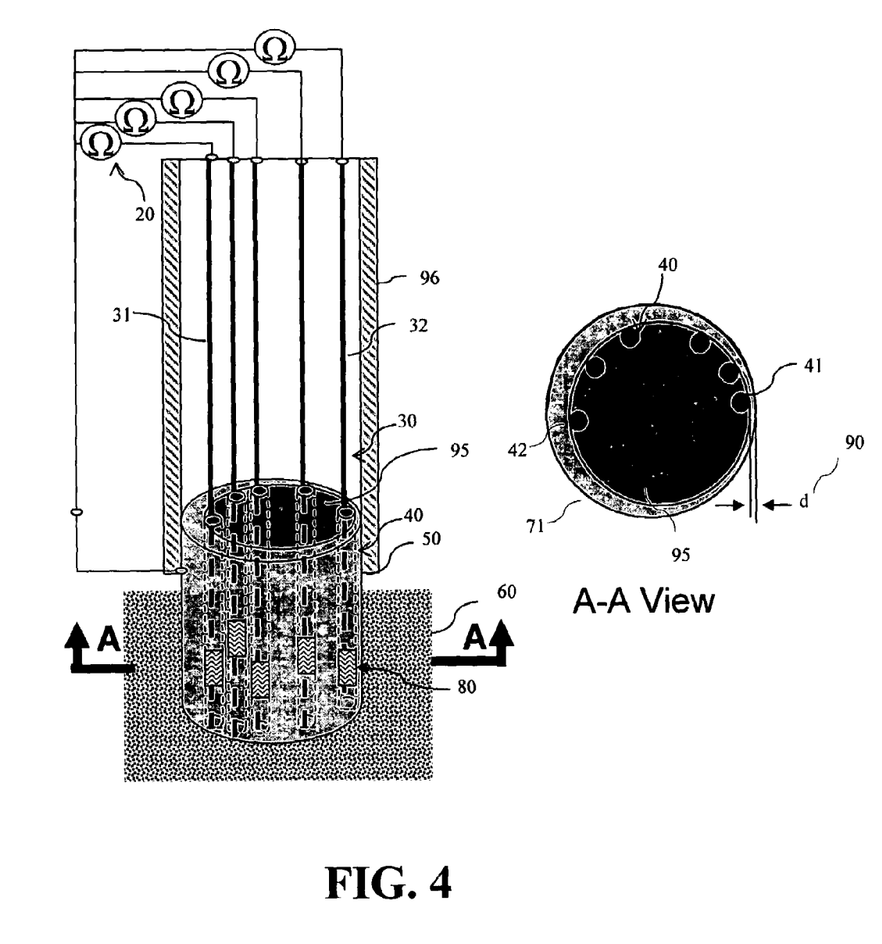
FIG. 4 illustrates the principle of a multihole corrosion sensor of circular surface with a long extension tube.

FIGS. 3 and 4

FIG. 3 is a variation of FIG. 1. A larger hole, non-concentric to the metal cylinder 50, is drilled vertically from the top to form a mug-shaped container, such that the thickness of the wall varies from one side to the other. The space in the container is filled with an epoxy or other sealant, except for the multiple holes 40. Therefore, the effective corrosion penetration depth (d) varies gradually from the first hole 41 to the last hole 42.

Compared with FIG. 1, only one precision hole is required, while FIG. 1 requires many precision holes.

Alternatively, the device shown in FIG. 3 can be made with a tube whose bottom end is sealed with epoxy, other sealants, or a weldment. The external diameter should be machined so that one side of the wall is thin and the other side of the wall is thick.

If a long tube 96 is used (see FIG. 4), the devices shown in FIGS. 1 through 3 can be used as a probe for insertion into a process stream or a pressurized vessel.

Figure 5:
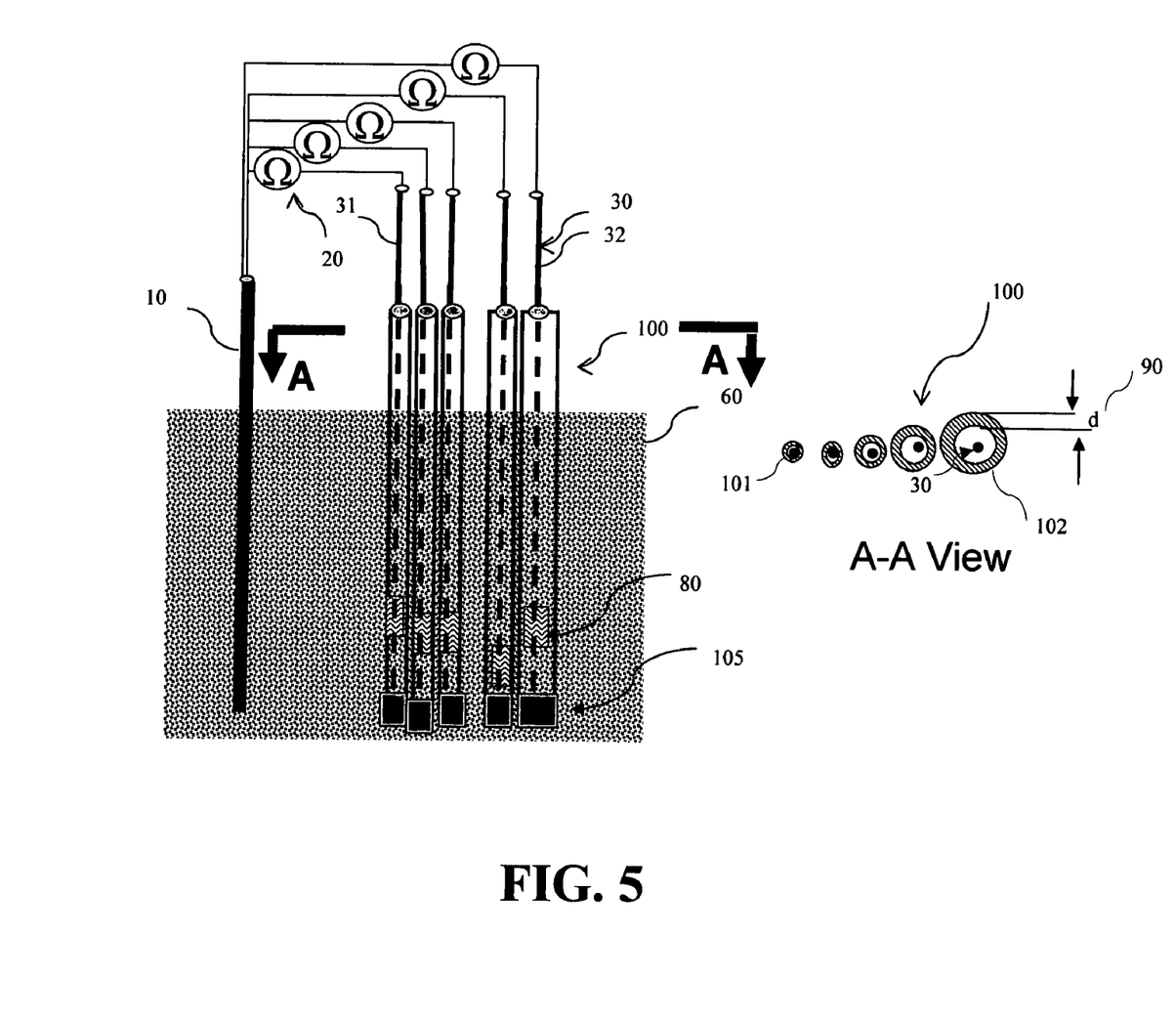
FIG. 5 illustrates the principle of a multihole corrosion sensor of tube design.

FIG. 5

FIG. 5 is another design of the multiple-hole sensor. In this design, multiple tubes 100—with varying wall thickness from the first tube 101 to the last tube 102, and sealed at the bottom with epoxy or other sealant or weldment 105—are used to house multiple electrodes 30.

Figure 6:
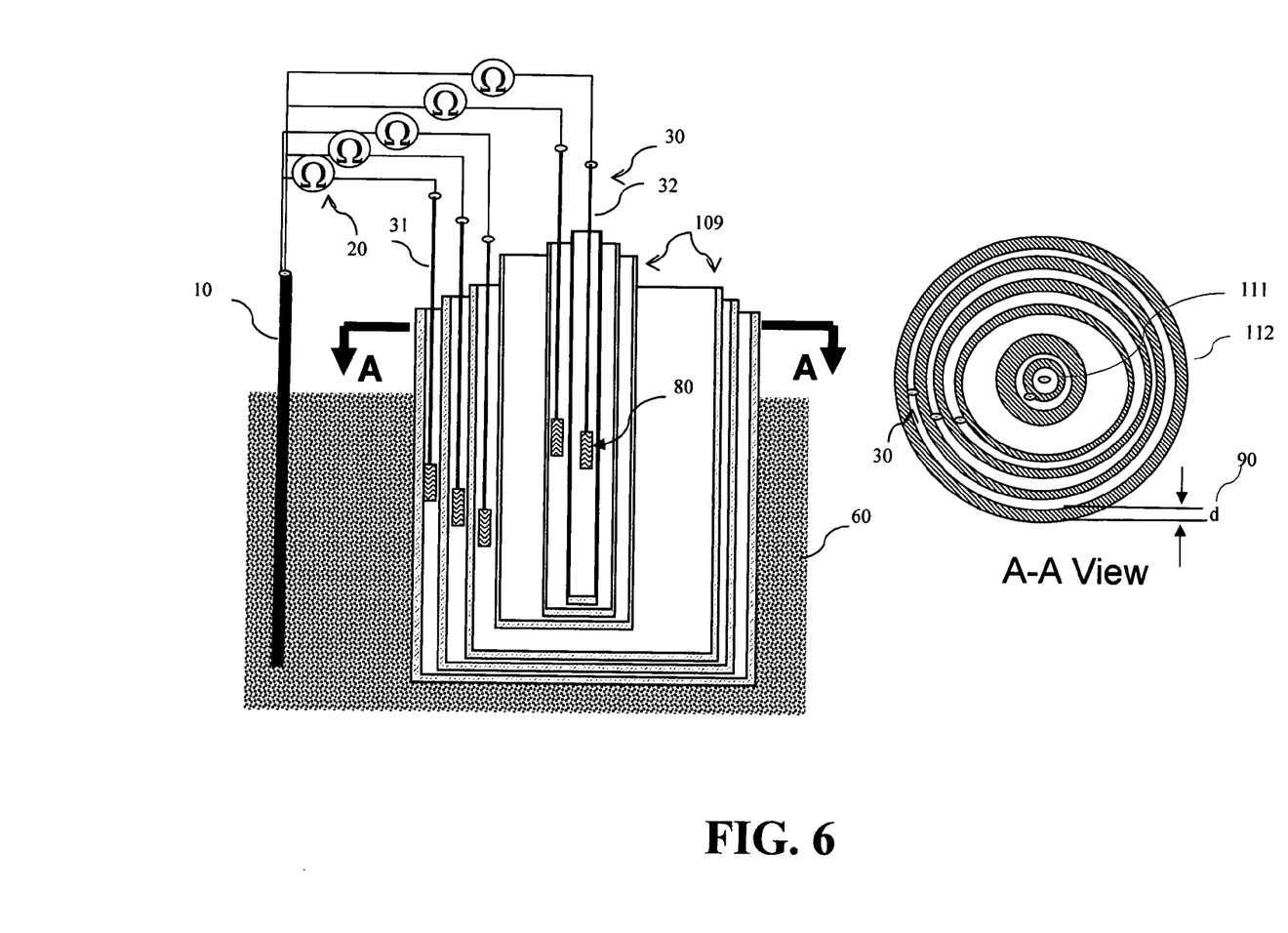
FIG. 6 illustrates the principle of a multihole corrosion sensor of layered-design.
Figure 7:
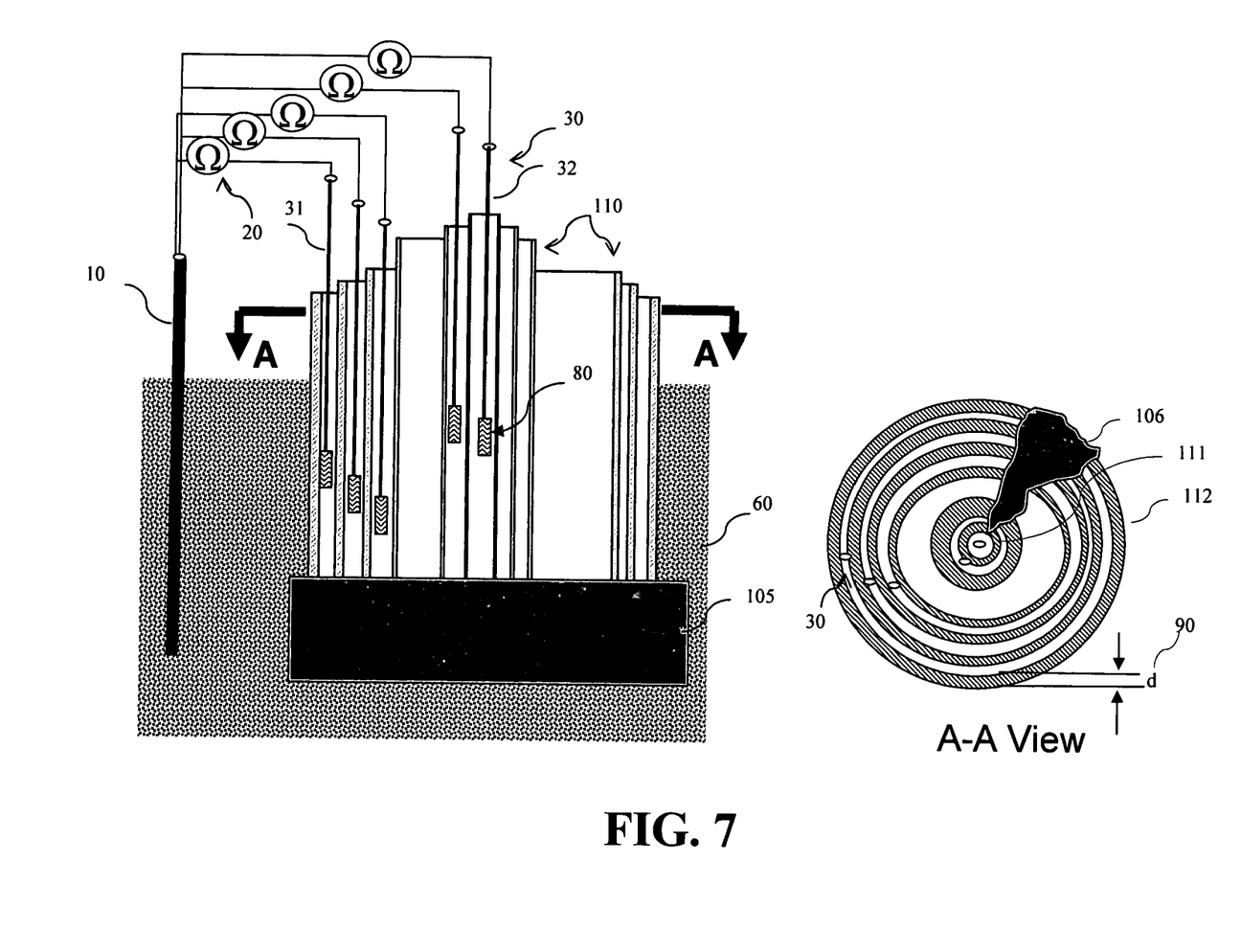
FIG. 7 illustrates the principle of a multihole corrosion sensor formed by spirally winding a piece of large foil into a cylindrical form.
Figure 8:
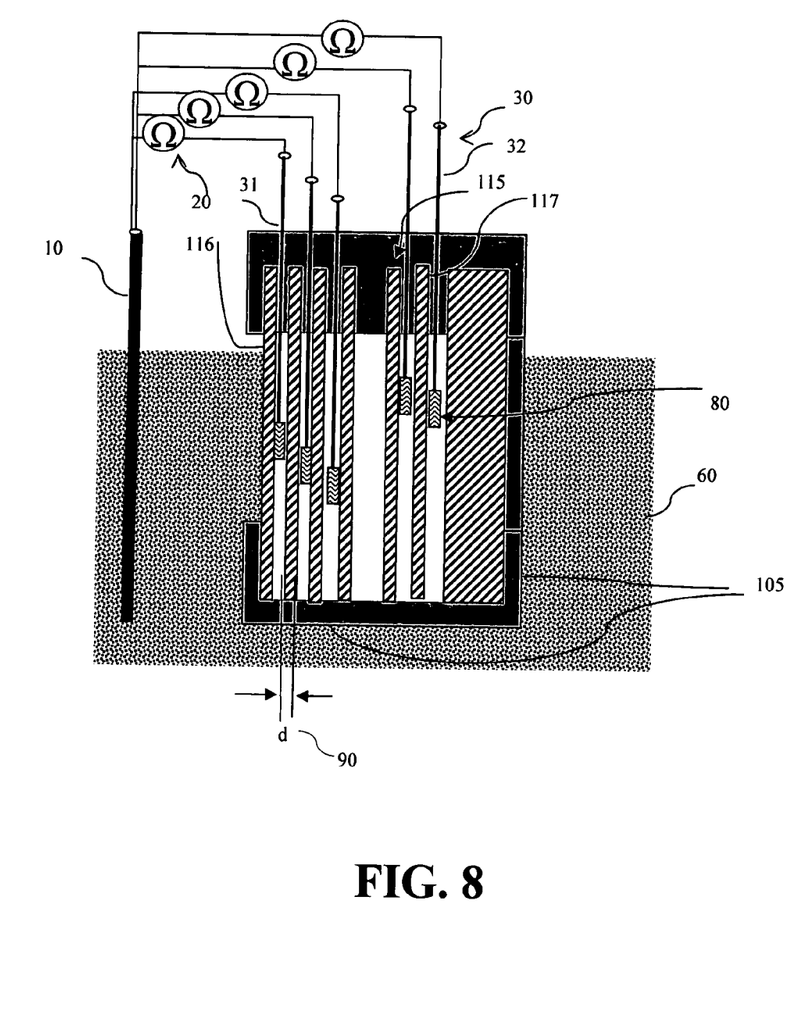
FIG. 8 illustrates the principle of a multihole corrosion sensor formed by multiple layers of foil discs.

FIGS. 6, 7 and 8

FIGS. 6, 7, and 8 are the layered-design of the multihole sensor. The corrosion penetration depth for the first electrode 31 is one layer of the wall of metal tubes 109 or 110 (FIGS. 6 and 7) or metal sheets 115 (FIG. 8), and the corrosion penetration depth for the last electrode 32 is the total wall thickness or total sheet thickness of all the metal tubes 109 or 110 or all the metal sheets 115.

The metal tubes in FIG. 6 have either a closed-end at the bottom or are sealed with epoxy or other sealants at the bottom. The metal tubes in FIG. 7 are made with foils or long sheets using epoxy or other sealant 105 and 106 to seal the bottom and the sides. The metal sheets in FIG. 8 can simply be small discs, squares, or rectangles that are glued or sealed together with epoxy or other types of sealing methods.

The metal tubes in FIG. 7 can also be formed by spirally winding a piece of large foil into a cylindrical form, but the space within each layer of the foil is sealed (separated) from the neighboring layers with epoxy or sealants 106. Such sealing is required to avoid having the liquid migrate from the space under one layer to the space under another layer.

Figure 9:
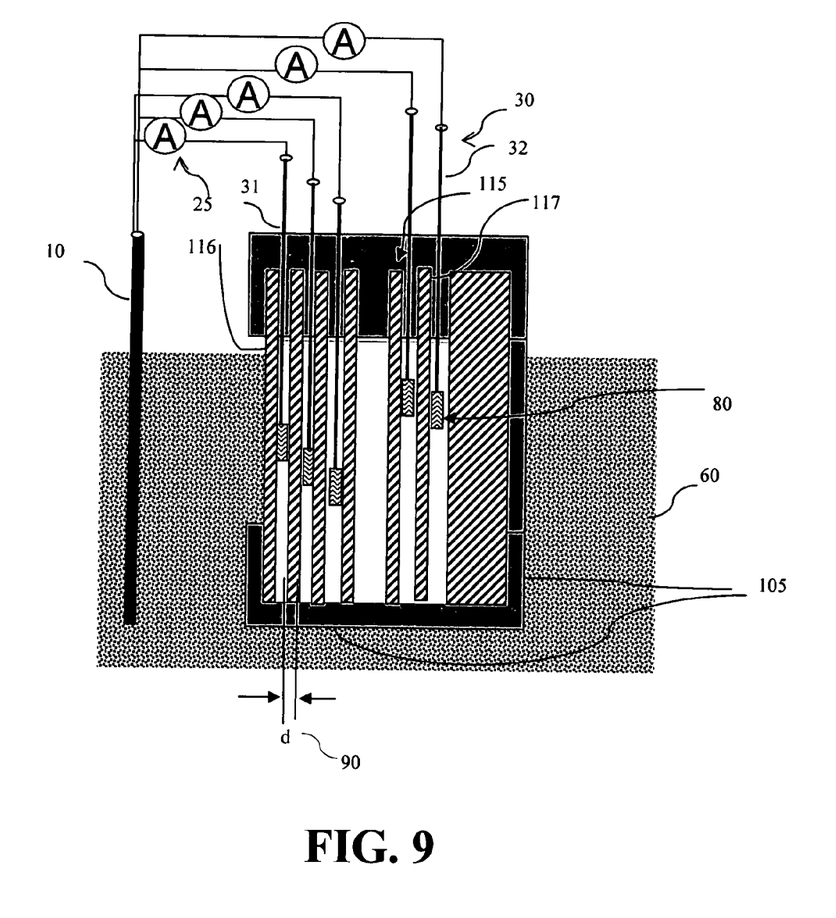
FIG. 9 illustrates the principle of a multihole corrosion sensor measured by ammeters.

FIG. 9

In the design of FIGS. 1 through 8, multiple ohm meters or multichannel impedance-measuring systems 20 are used. FIG. 9 shows that ammeters, zero-resistance ammeters or other types of current-measuring units 25 may be used to replace the impedance-measuring system 20. If an electrode (one of 30) is in contact with the corrosive medium 60 due to corrosion damage to the metal, a galvanic current will be generated between this electrode and the common electrode 10. This is especially true if the common electrode 10 is made of a different metal from the electrodes 30. Alternatively, the common electrode 10 may be polarized by an external power source so that there would be a strong current signal through the electrodes that are in contact with the corrosive medium (electrolyte) caused by corrosion.

Figure 10:
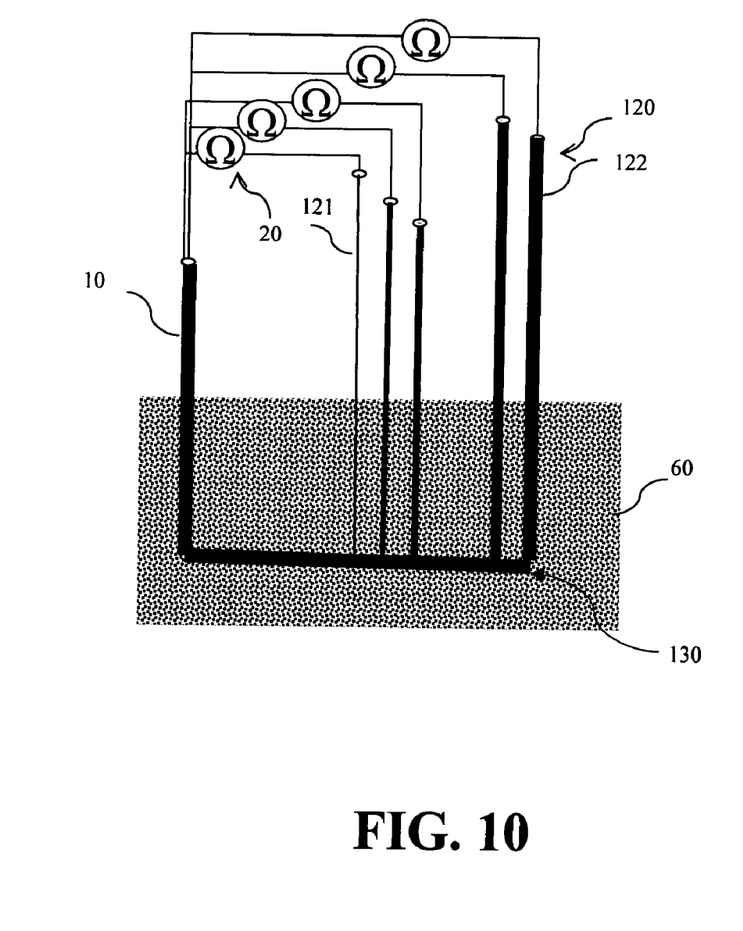
FIG. 10 illustrates the principle of a multiwire corrosion sensor measured with ohm meters.
Figure 11:
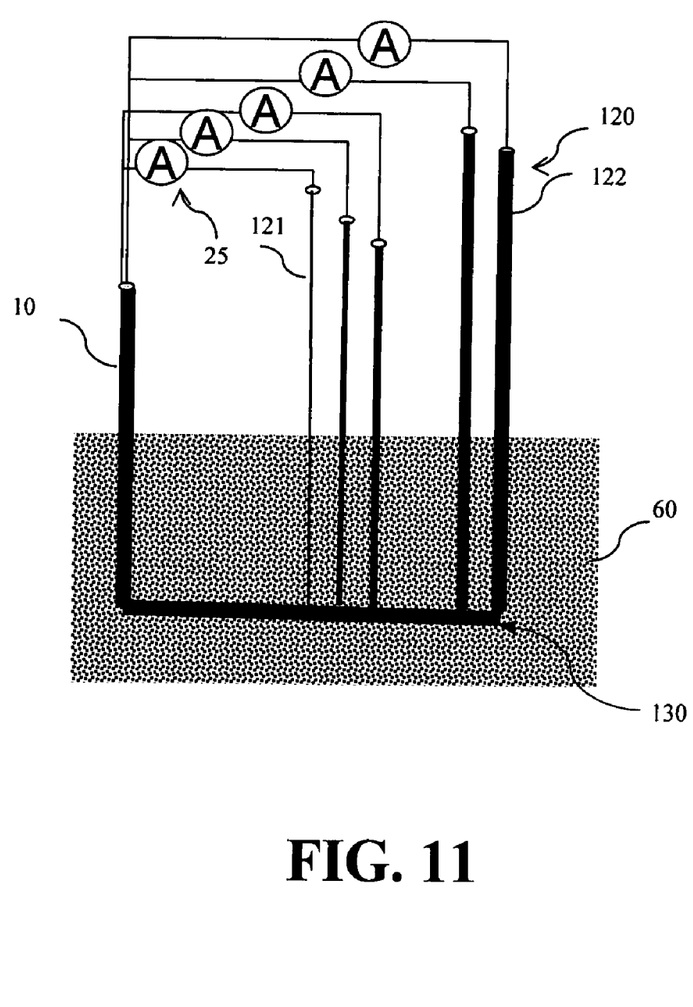
FIG. 11 illustrates the principle of a multiwire corrosion sensor measured with ammeters.
Figure 12:
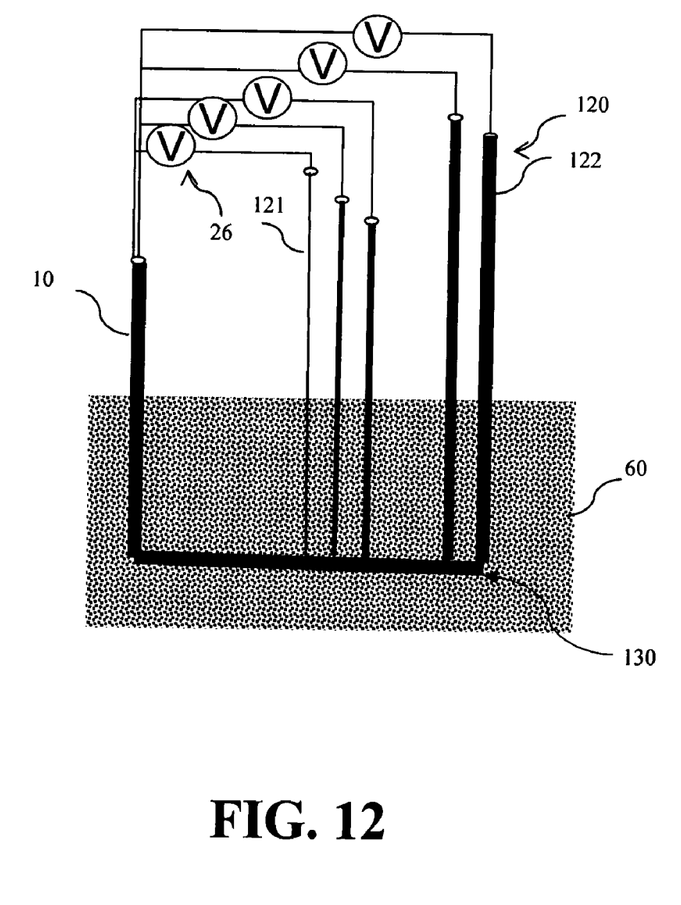
FIG. 12 illustrates the principle of a multiwire corrosion sensor measured with voltmeters.

FIGS. 10, 11 and 12

FIGS. 10, 11, and 12 show the multiwire sensors for localized and general corrosion monitoring. The multiple metal wires 120 are made of the same metal whose corrosion rate is to be measured. The sizes of the wires increase from the first wire 121 to the last wire 122.

In FIG. 10, each wire is connected, at one end, to a common electrode 140. An ohmmeter, an impedance-measuring unit, or one channel of a multichannel unit 20 is used to measure the impedance between the common electrode and the other end of each electrode. All of these wires and the common electrode are exposed to a corrosive medium 60. The principle of this type of sensor is that when a wire is significantly corroded or totally corroded, the resistance between the other end of the wire and the common electrode significantly increases. This type of sensor is suitable for both localized and general corrosion. For localized corrosion, a single pit on a wire will break the wire, if its size is the same as the diameter of the wire, and will cause the ohm meter 20 to respond.

In FIG. 11, the impedance-measuring units, as shown in FIG. 10, are replaced by a current-measuring unit 25. When the wires are connected to the common electrode 140, no current will flow through the current-measuring unit 25; when a wire is broken due to corrosion, galvanic current will flow through the corresponding current-measuring unit or the corresponding channel of a current-measuring unit. As in the discussions for FIG. 9 (above), this is especially true when the common electrode is made of a different type of metal from wires 120.

In FIG. 12, the impedance-measuring units, as shown in FIG. 10, are replaced by a voltage-measuring unit 26. When the wires are connected to the common electrode 10, the voltage readings should be zero; when a wire is broken, due to corrosion, the wire will be at its corrosion potential, and the corresponding voltage-measuring unit—or the corresponding channels of a voltage-measuring unit—would indicate the potential difference between the electrode and the common electrode 10. This is especially true when the common electrode is made of a different type of metal from the metal wires 120.

Figure 13:
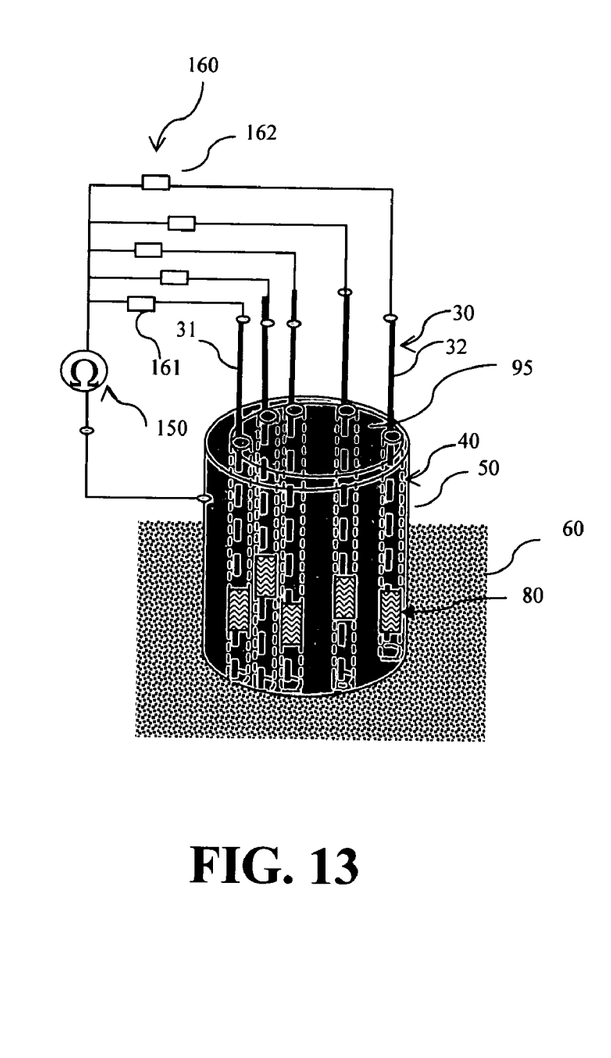
FIG. 13 illustrates the principle of a multihole corrosion sensor measured with a single impedance meter.
Figure 14:
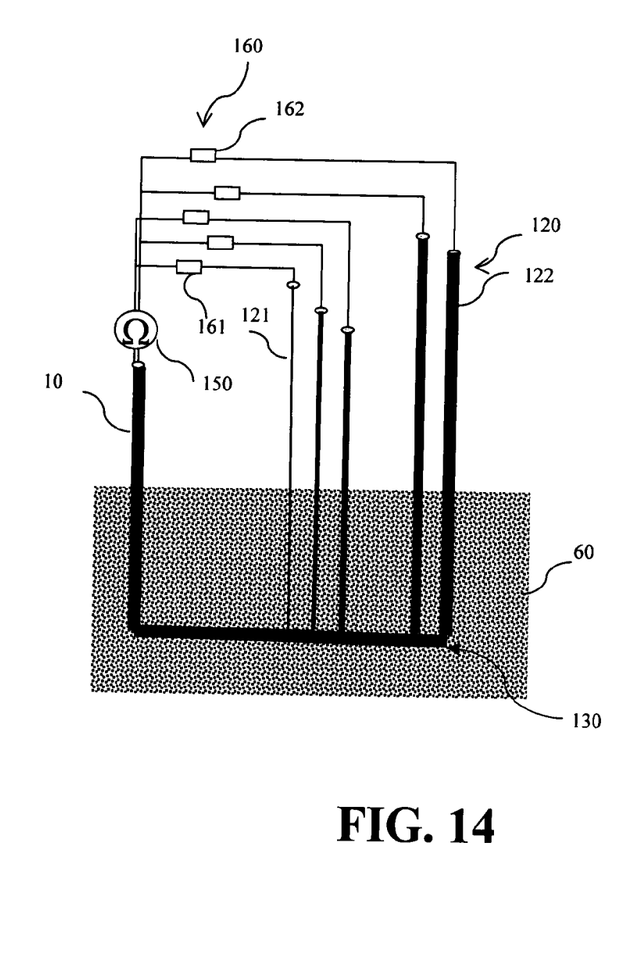
FIG. 14 illustrates the principle of a multiwire corrosion sensor measured with a single impedance meter.
Figure 15:
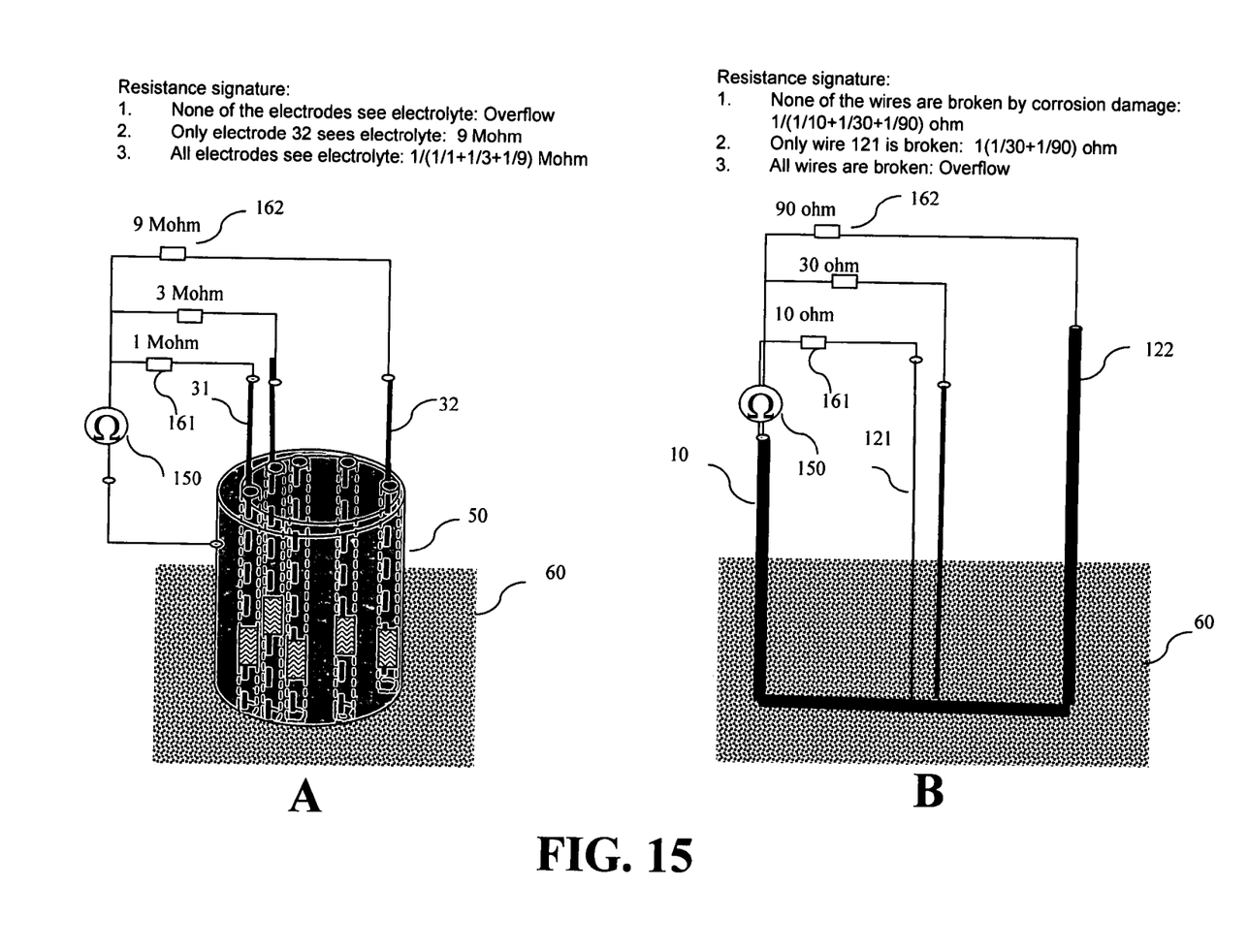
FIG. 15 illustrates the impedance signatures from a multiwire or a multihole corrosion sensor measured with a single impedance meter.

FIGS. 13, 14 and 15

FIGS. 13 and 14 show that a single impedance-measuring device 150 may be used to replace the multiple impedance-measuring devices or the multichannel impedance-measuring device as discussed in the forgoing sections. The use of a single unit would substantially reduce the cost of the sensor system.

In FIGS. 13 and 14, each of the multiple electrodes 30 or multiple wires 120 is connected to the single impedance-measuring unit 150 through an impedance box (a combination of resistors, capacitors or inductors) with a unique signature of impedance. The unique signature of the impedance box allows the identification of the electrode or electrodes that are surrounded by electrolyte due to corrosion damage to the wall of the metal of interest 50, or identification of the wire or wires that are broken due to corrosion damage.

FIG. 15 presents both an example for the impedance boxes in the multihole sensor and an example for the impedance boxes in the multiwire sensor, respectively. In these two examples, only three electrodes or wires are shown. Because the resistors are in parallel, the resistance values measured by the impedance-measuring device 150 under different conditions (after omitting the impedance of solution and the impedance at the electrode/electrolyte interfaces) for FIG. 15A are:

1. None of the electrodes see electrolyte: Overflow
2. Only electrode 32 sees electrolyte: 9 Mohm
3. All electrodes see electrolyte: 1/(1/1+1/3+1/9) Mohm Similarly, for FIG. 15B, the resistance values measured by the impedance-measuring unit 150 under different conditions are (assuming impedance of solution and the impedance at the broken electrode/electrolyte interfaces are relatively large):

1. None of the wires are broken by corrosion damage: 1/(1/10+1/30+1/90) ohm
2. Only wire 121 is broken: 1(1/30+1/90) ohm
3. All wires are broken: Overflow For FIG. 15A, if the electrolyte (corrosion medium 60) is highly conductive, the real part of the impedance between the electrodes 30 and the main body of the metal of interest 50 is usually much lower than 1 Mohm and it is reasonable to omit them. However, for measurement in weak electrolyte, the real part of the impedance between the electrodes 30 and the main body of the metal of interest 50 may be high. An additional electrode may be used to measure such impedance value. This impedance value can be used as the baseline to compensate for the impedances measured for the other electrodes by the impedance-measuring unit 150. Similarly, the impedance of solution and the impedance at the broken electrode/electrolyte interfaces may be compensated if they are not large.

OTHER EMBODIMENTS

Although the present invention has been described in detail, it should be understood that various changes, substitutions, and alterations can be made hereto, without departing from the spirit and scope of the invention as defined by the appended claims.

The invention claimed is:

1. A method of using multihole corrosion sensor to measure the corrosion penetration rate, comprising:
   exposing the sensor to the corrosion medium of interest;

wherein the sensor has a plurality of electrodes embedded in individual cavities that are formed by one or more pieces of metal of interest and have different values of known effective wall thickness, such that the external surface of the wall is exposed to the corrosion medium, and such that each electrode is electrically isolated from other electrodes and properly sealed, so that it contacts only with the corrosion medium leaking through the wall of the cavity in which the electrode resides after the wall of the cavity is perforated by corrosion;

wherein each electrode is connected to a common electrode exposed to the same corrosion medium, such that an electrical path will be formed between the common electrode and the electrode that has contact with the corrosion medium;

measuring the electrical signal, from an electrical readout device connected between each electrode and the common electrode, which responds to the perforation of the cavity wall surrounding the electrode;

determining the time it takes for the electrical signal to change from the initial state;

determining which electrode causes the signal change and the effective thickness of the wall surrounding the electrode;

calculating the corrosion penetration rate of the metal, using the effective wall thickness and the time it takes for the electrical signal to change.

2. The method of claim 1, wherein the common electrode is the wall of the metal itself.

3. The method of claim 1, wherein the electrical readout device is an ohmmeter.

4. The method of claim 1, wherein the electrical readout device is an ammeter.

5. The method of claim 1, wherein the electrical readout device is a voltmeter.

6. The method of claim 1, wherein each cavity is formed by a single metal with different wall thickness and the effective wall thickness is the thickness of the metal wall.

7. The method of claim 6, wherein the cavities are formed by multiple tubes with different wall thicknesses.

8. A method of claim 1, wherein the cavities are the holes drilled in a one-piece metal with a flat or a circular surface for exposure to the corrosion medium such that the holes are in parallel with the flat or circular surface.

9. A method of claim 1, wherein the cavities are formed using a sealing material on one side of a layer of metal that has varying thickness from one location to the other location, and the other side of the layer is exposed to the corrosion medium such that the cavities at different locations have different values of known wall thickness of the metal of interest.

10. A method of claim 9, wherein both sides of the layer of metal are in circular form.

11. The method of claim 1, wherein the cavities are formed by one or more layers of a metal of interest and the effective wall thickness for a cavity that is surrounded by or behind many layers of the metal is the sum of all the layers surrounding the cavity.

12. The method of claim 11, wherein the cavity is formed by multiple tubes with different inside diameters and the small-diameter tubes are in the large-diameter tubes so that the effective wall thickness for an inner cavity is the sum of the thickness of the tube walls surrounding the inner cavity.

13. The method of claim 11, wherein the cavity is formed by spirally winding a piece of large foil into a cylindrical form.

14. The method of claim 1, wherein the electrical readout devices between the common electrode and each of the electrodes are replaced by a single electrical readout device and an impedance box that has a unique signature is connected between each electrode and the single electrical readout device, such that it allows the determination for which electrode causes a signal change measured by the electrical readout device.

15. A method of using a multiwire corrosion sensor to measure the corrosion penetration rate, comprising:

exposing the sensor to the corrosion medium of interest;

wherein the sensor has a plurality of wires that are made of a metal of interest, have different values of known cross-sectional dimensions, and are exposed to the corrosion medium;

wherein one end of each wire is connected to a common electrode exposed to the same corrosion medium, such that a low resistance electrical path is formed between the common electrode and the wire;

measuring the electrical signal, from an electrical readout device connected between the common electrode and the other end of each wire, which responds to the thinning of the wire;

determining the time it takes for the electrical signal to change significantly from the initial state;

determining which wire that causes the change and the cross-sectional dimension of the wire;

calculating the penetration rate, using the cross-sectional dimension and the time it takes for the signal to change.

16. The method of claim 15, wherein the electrical readout device is an ohmmeter.

17. The method of claim 15, wherein the electrical readout device is an ammeter.

18. The method of claim 15, wherein the electrical readout device is a voltmeter.

19. The method of claim 15, wherein the individual electrical readout devices between the common electrode and each of the wires are replaced by a single electrical readout device and an impedance box that has a unique signature is connected between each wire and the single electrical readout device, such that it allows the determination for which electrode causes a signal change measured by the electrical readout device.

* * * * *